US012624328B2

(12) United States Patent     (10) Patent No.:    US 12,624,328 B2
Raviv et al.                        (45) Date of Patent:       May 12, 2026

(54) SYSTEM FOR 3D CULTIVATION OF PLANT CELLS AND METHODS OF USE

(71) Applicant: PLURI BIOTECH LTD., Haifa (IL)

(72) Inventors: Lior Raviv, Kfar Monash (IL); Eran Ben Eliezer, Kiryat Tivon (IL)

(73) Assignee: PLURI BIOTECH LTD., Haifa (IL)

( * ) Notice: Subject to any disclaimer, the term of this patent is extended or adjusted under 35 U.S.C. 154(b) by 0 days.

(21) Appl. No.: 18/726,116

(22) PCT Filed: Mar. 18, 2024

(86) PCT No.: PCT/IL2024/050278
§ 371 (c)(1),
(2) Date: Jul. 2, 2024

(87) PCT Pub. No.: WO2024/252382
PCT Pub. Date: Dec. 12, 2024

(65) Prior Publication Data
US 2025/0115845 A1     Apr. 10, 2025

(30) Foreign Application Priority Data
Jun. 8, 2023     (IL) .......................................... 303555

(51) Int. Cl.
*C12M 1/12*          (2006.01)
*C12M 1/00*          (2006.01)
(Continued)

(52) U.S. Cl.
CPC ............ *C12M 25/18* (2013.01); *C12M 23/04* (2013.01); *C12M 27/02* (2013.01); *C12M 29/14* (2013.01);
(Continued)

(58) Field of Classification Search
CPC ...... C12M 25/18; C12M 23/04; C12M 27/02; C12M 29/14; C12M 35/04; C12M 41/12;
(Continued)

(56) References Cited

U.S. PATENT DOCUMENTS 5,705,390  A     1/1998   Kadouri et al.
5,998,184  A    12/1999   Shi
(Continued)

FOREIGN PATENT DOCUMENTS

CN       115595263  A      1/2023
DE         3801477  A1     8/1989

OTHER PUBLICATIONS

Notice of Deficiencies for U.S. Pat. No. 303555, Nov. 19, 2023.
(Continued)

*Primary Examiner* — Michael L Hobbs
*Assistant Examiner* — Lenora A Abel
(74) *Attorney, Agent, or Firm* — GREENBERG TRAURIG, LLP

(57)                    ABSTRACT

This invention is directed to a method for three-dimensional cultivation of proliferating plant cells in a packed bed bioreactor, the bioreactor comprising at least one packed bed chamber configured to confine said proliferating plant cells within it such that the proliferating plant cells become a three-dimensional stationary biomass phase; and At least one container comprising a fluid media, the fluid media is configured to flow through said proliferating plant cells stationary biomass phase, wherein, the flow of the fluid media through the proliferating plant cells stationary biomass phase allows transfer of compounds from the fluid media into the cells and vice versa in low shear forces within the at least one packed bed chamber thereby imitating natural growth environment of the proliferating plant cells within the 3D bioreactor.

19 Claims, 9 Drawing Sheets

(51) Int. Cl.
　　 *C12M 1/06* 　　　　 (2006.01)
　　 *C12M 1/34* 　　　　 (2006.01)
　　 *C12M 1/42* 　　　　 (2006.01)
　　 *C12N 5/04* 　　　　 (2006.01)

(52) U.S. Cl.
　　 CPC ............ *C12M 35/04* (2013.01); *C12M 41/12* (2013.01); *C12M 41/26* (2013.01); *C12M 41/32* (2013.01); *C12M 41/34* (2013.01); *C12N 5/04* (2013.01); *C12N 2513/00* (2013.01)

(58) Field of Classification Search
　　 CPC ...... C12M 41/26; C12M 41/32; C12M 41/34; C12N 5/04; C12N 2513/00
　　 USPC ...................................................... 435/289.1
　　 See application file for complete search history.

(56) References Cited

U.S. PATENT DOCUMENTS

| | | | |
|---|---|---|---|
| 2010/0112700 | A1 | 5/2010 | Shaaltiel et al. |
| 2011/0263021 | A1 | 10/2011 | Stobbe |
| 2014/0193901 | A1 | 7/2014 | Lee et al. |
| 2014/0227769 | A1* | 8/2014 | Strobbe .................... C12N 9/00 |
| | | | 435/287.1 |
| 2017/0037421 | A1 | 2/2017 | Blessing et al. |
| 2022/0033751 | A1 | 2/2022 | Raviv et al. |
| 2022/0046883 | A1 | 2/2022 | Yanay et al. |

OTHER PUBLICATIONS

Applicant response to notice of objections in accordance with regulation 42 for U.S. Pat. No. 303555, Feb. 21, 2024.

Amended reply to examiner's report for U.S. Pat. No. 303555, Feb. 22, 2024.

Application accepted for second publication for U.S. Pat. No. 303555, Feb. 25, 2024.

Notice before acceptance of patent application for U.S. Pat. No. 303555, Feb. 25, 2024.

Patent Certificate for U.S. Pat. No. 303555, Jun. 3, 2024.

* cited by examiner

SYSTEM FOR 3D CULTIVATION OF PLANT CELLS AND METHODS OF USE

FIELD OF THE INVENTION

This invention is in the field of plant cells culturing in general and directed to plant cells culturing in a packed bed bioreactor in particular.

BACKGROUND

The climate change and the constantly increasing world population leads to a real concern and fear that traditional farming methods will not be able to meet the anticipated growth in food demands, with amount of arable land per capita available for food production decreasing due to factors such as urbanization, erosion, soil salinization, and desertification. Furthermore, sustainability in food production and the threat of crop losses due to climate change and plant diseases are playing an increasingly important role and need to be taken into account. Therefore, various alternative agricultural strategies are constantly being considered.

Plants are an essential component to produce carbohydrates, lipids (fatty acids), proteins (amino acids), and vitamins and have been drawing attention for the biotechnology industry with the production of secondary metabolites and recombinant proteins. Secondary metabolites are usually small but complex molecules, which are in many cases impossible or expensive to synthesize chemically. Based on their metabolic pathways and their biogenetic precursors, they can be classified into three groups: terpenoids (e.g., paclitaxel, ginsenosides), alkaloids (e.g., morphine) and phenolics (e.g., shikonin, rosmarinic acid). The extraction of secondary metabolites from plants, which were traditionally grown in fields, is still the main production method for these substances. However, as per the above, there are a number of disadvantages associated with traditional farming and the excessive variation of environmental conditions over time and region, which leads to unpredictable differences in the quality and quantity of the raw materials. Many secondary metabolites are produced in plants that are not suited to agricultural production or can be hard to grow outside their local ecosystems. As a result, it is not surprising that around one fifth of the 50,000 medical plants that are used today are on the list of threatened species. Therefore, plant cell and tissue cultures grown in bioreactors offer an eco-sustainable alternative. Furthermore, plant cell and tissue cultures are believed to represent an appropriate method that addresses the main drawbacks of traditional farming of herbs and avoids the problems associated with extracting products from protected wild plants. One popular example of a pharmaceutically used secondary metabolite derived from plant cell cultures is paclitaxel, an anti-cancer drug. Previously produced by harvesting the bark from *Taxus* sp. trees, today, the large-scale production of paclitaxel is performed in stainless steel bioreactors. Furthermore, the complete elimination of environmental variations leads to improved consistency between batches, which is crucial for gaining official acceptance. The avoidance of labor-intensive greenhouse or field production of whole plants reduces costs, not only in upstream processing, but also in downstream processing, in particular the case of products which are secreted into the medium. Obviously, the safety of the process with regards to product contamination with endotoxins and mycotoxins and, of no less importance, with regards to environmental contamination with artificial, genetically modified plants is tremendously enhanced when operating in a closed bioreactor system.

Thus, the present invention is aimed to provide a possible cost and time effective solution by cultivating plant cells in a packed bed bioreactors in a proprietary method that mimics the natural environment of the plant. The system and methods disclosed herein may be applicable to all and/or most plant species and may be used for cultures may present a possible solution, as they allow for controlled, closed and sustainable manufacturing of plant based products that are used in various industries such as food, pharmaceuticals, cosmetics and else.

SUMMARY OF THE INVENTION

In one main aspect, the present invention is directed to a three-dimensional (3D) bioreactor for cultivating proliferating plant cells comprising at least one packed bed chamber configured to confine said proliferating plant cells within it such that the proliferating plant cells become a three-dimensional stationary biomass phase; and at least one container comprising a fluid media, the fluid media is configured to flow through said proliferating plant cells stationary biomass phase; wherein, the flow of the fluid media through the proliferating plant cells stationary biomass phase allows transfer of compounds from the fluid media into the cells and vice versa in low shear forces within the at least one packed bed chamber thereby imitating natural growth environment of the proliferating plant cells within the 3D bioreactor.

For clarification purposes the term "culturing" as used herein means maintaining the plant cells in conditions suitable for growth/metabolite production.

The term "harvesting" as used herein includes the extraction of cells from a bioreactor or separating cell content from the cells during or following the culturing period.

The term "compounds" as used herein includes primary and secondary metabolites.

The term "plant-based metabolites compounds" as used herein includes primary or secondary metabolite. Some non-limiting examples of plant-based metabolites include amino acids, sugars, organic acids, phenols, alkaloids, terpenes and flavonoids.

The terms "plant cell/s", "plant cells biomass", "plant cells callus", "callus", "aggregates", "plant cells aggregates", "plant cells culture", "plant culture" and "plant cells callus" may be used interchangeably and are all directed to describe plant cells.

The term "suspension culture" refers to a culture in which the plant cells are exposed to conditions that are compatible with cell proliferation and growth and allow the cells to grow in suspension.

The terms "three-dimensional culture" and "3D culture" refer to a culture in which the plant cells are exposed to conditions that are compatible with cell growth and allow the cells to grow in a 3D orientation relative to one another. Such conditions will typically utilize a 3D growth surface (also referred to as a "scaffold", "carrier" or "3D substrate"), in some embodiments comprising an adherent material, which is present in the 3D culture vessels. Preferably, 3D culture is performed in conjunction with the described modular apparatus.

In some optional embodiments, the bioreactor may further comprise at least one monitoring and/or a controlling unit/s for monitoring and/or controlling at least one parameter of the culturing conditions and media parameters. None limiting examples of parameters that may be monitored and/or controlled are pH, temperature, stirring velocity, flow rate, gases concentration, amino acids levels, vitamins levels, minerals levels, growth factors levels, dissolved oxygen levels, glucose levels, lactate levels, lactate dehydrogenase levels, NH.sub.3 levels, glutamate levels, or combinations thereof.

Optionally but not necessarily, the fluid media may be a growth media that provides nutrients to the proliferating plant cells, and uptakes plant cells metabolites and secreted compounds from the plant cells into the growth media. Other fluid media may also be used according to the plant cells type and the desired application.

In some specific embodiments, the fluid media may be exchanged to either one of a differentiating media, a maturation media, and an elicitation media, and combinations thereof in any order, so as to allow a consecutive development of the plant cells and imitate the natural growth process of plant cells within the 3D bioreactor.

The bioreactor, in some embodiments may further comprise at least one inlet port to allow addition of gases and/or liquids and/or solid material into the 3D bioreactor during the cultivation of the proliferating plant cells.

In yet further embodiments, the bioreactor may further comprise at least one outlet port to allow removal of fluid media out from the 3D bioreactor during the cultivation of the proliferating plant cells for collecting metabolites secreted by the proliferating plant cells stationary biomass phase during the cultivation process and/or for removing plant's secreted compounds/metabolites and/or for balancing the fluid media parameters.

Optionally, the bioreactor may further comprise vibrating arms functionally connected to the packed bed chamber, so as to allow vibrating of the proliferating plant cells for minimizing channeling effect and improving contact between the fluid media and the proliferating plant cells stationary biomass phase, and/or for harvesting said proliferating plant cells stationary biomass phase for either collecting the cells or for lysing the cells to obtain their content. The harvesting of the plant cells may be obtained by combining enzymatic reaction and applying vibration force on the plant cells so as to lyse the cells and collect their content from the media.

The packed bed chamber may be positioned within the container having the flowing fluid media or it may be positioned outside the container having the fluid media, and connected to it by tubes that flow the fluid media through said proliferating plant cells stationary biomass phase.

In some embodiments, the packed bed chamber is divided into one or more sub-chambers by at least one perforated disk, such that each sub-chamber contains proliferating plant cells biomass cells either in a similar size or in gradient sizes according to the hole dimensions of the at least one perforated disk.

Optionally, the at least one packed bed chamber comprises carriers configured to allow the proliferating plant cells to grow within them and/or on top of them.

In some optional embodiments of the invention, the bioreactor further comprises a stirring mechanism functionally connected to the packed bed chamber and configured to bland the proliferating plant cells stationary biomass phase within the basket, so as to rearrange the plant cells biomass and to allow fluent flow of the media through the plant cells.

The stirring mechanism may comprise at least a large gear attached to a stirrer, said stirrer is positioned within the packed bed chamber, and a small gear attached to a handle.

Yet, in some embodiments, the packed bed chamber is a separated chamber from the fluid media container and the plant cells stationary biomass phase is used in agriculture for seeding the stationary cells biomass to obtain plants or parts thereof.

Optionally, the plant cells stationary biomass phase is harvested for collecting compounds produced by the plant cells stationary biomass phase. The compounds may be used for industrial applications. Some none limiting examples of industrial applications are food manufacturing, medicaments, industrial applications, and cosmetic compositions.

In yet, further embodiments of the invention, the bioreactor may further comprise a perfusion chamber containing a 3D packed bed substrate containing one or more macro carriers, microcarriers, or combinations thereof.

This invention is further directed to a method for cultivating proliferating plant cell for usage of the plant cells and/or compounds produced by said plant cells for medical, cosmetic, food tech, agriculture, and industrial applications using the bioreactor disclosed above.

In one specific embodiment, this invention is directed to a method for cultivating proliferating plant cells in a 3D bioreactor comprising the following steps: a) confining proliferating plant cells within at least one packed bed chamber such that the proliferating plant cells become a stationary biomass phase; and b) flowing media through said proliferating plant cells stationary biomass phase, from at least one container comprising a fluid media; wherein, the flow of the fluid media through the proliferating plant cells stationary biomass phase allows transfer of compounds from the fluid media into the cells and vice versa in low shear forces within the at least one packed bed chamber thereby imitating natural growth environment of the proliferating plant cells within the 3D bioreactor.

Optionally, the method for cultivating proliferating plant cells described above may further comprising a step of c) monitoring and/or controlling at least one parameter of the culturing conditions and media parameters by at least one monitoring and/or a controlling unit/s.

Also provided herein a method for cultivating proliferating plant cell for usage of the plant cells and/or compounds produced by the plant cells for medical, cosmetic, food tech, agriculture, and industrial applications using the bioreactor of the invention as described above, the method comprising: a) inputting proliferating plant cells onto at least one packed bed chamber in a bioreactor, wherein said packed bed chamber confines the proliferating plant cells within said packed bed chamber such that the proliferating plant cells create a stationary biomass phase; and b) flowing at least one fluid media from at least one container comprising a fluid media through the stationary biomass phase in a low-shear environment, allowing for efficient transfer of compounds between the fluid and the cells, wherein said fluid media contains one or more of nutrients, hormones, plant growth regulators (PGRs), vitamins, amino acids, trace elements, or combinations thereof.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 5A is a schematic partial view illustration of a 3D mini packed bed bioreactor illustrating the growth of plant cell aggregates on top of scaffolds within a growing basked. The plant cells aggregates are filling the growing basket and remain within the basked thanks to the upper and bottom perforated disks that mechanically limit their ability to exit from the basket into the medium on top or below basket. FIGS. 5B-5C are pictures showing *Cannabis* cells embedded in 3D carriers. The pictures were made with Blue Hoechst staining. FIG. 5D schematically illustrates plant cells seeding and growth in a 3D mini bio system without carriers. FIG. 5E is a close-up pictorial illustration of a *Cannabis* cell culture aggregate adherence to 3D carriers.

DETAILED DESCRIPTION OF EMBODIMENTS OF THE INVENTION

Figure 1A:
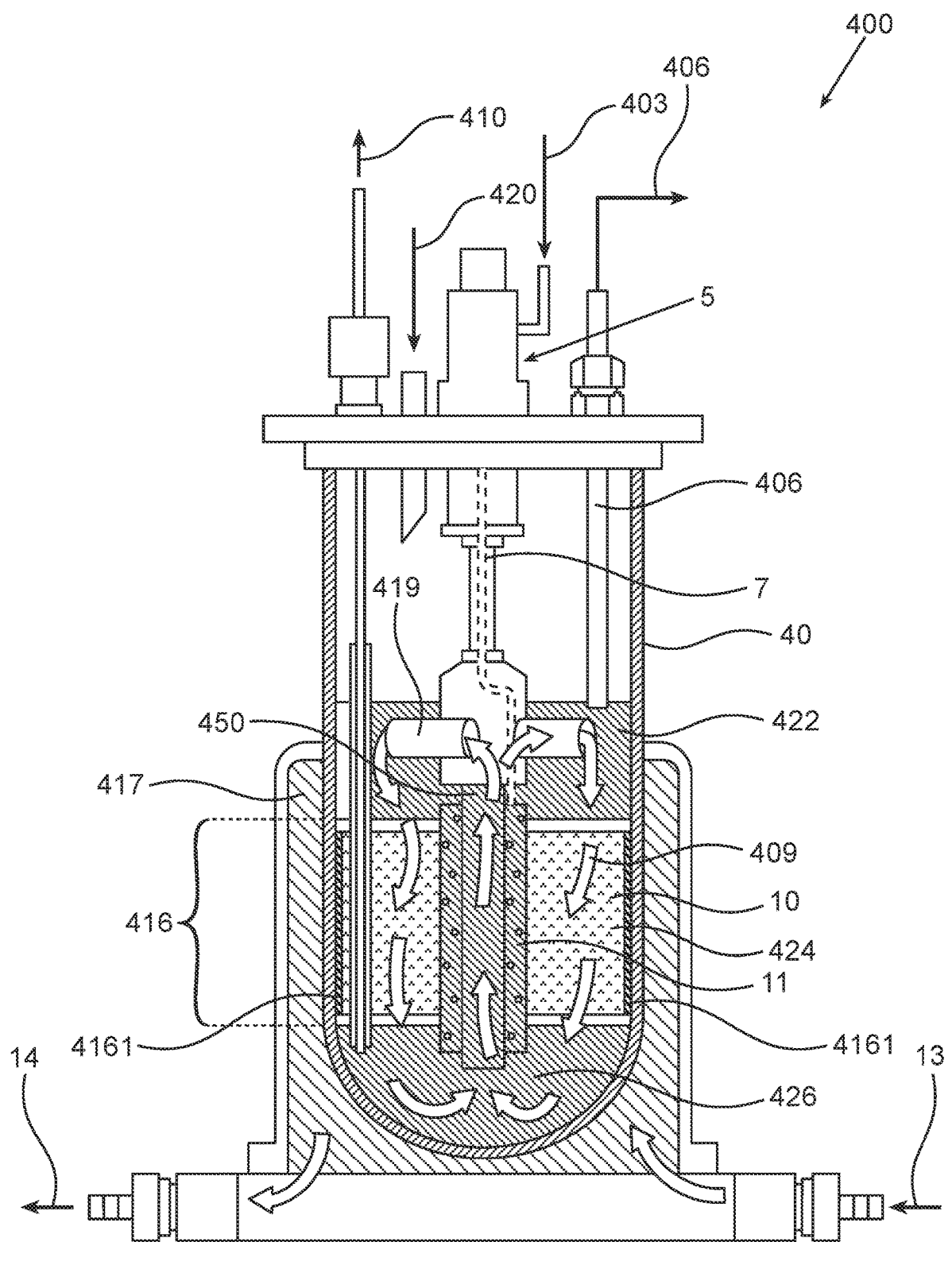
FIG. 1A is a schematic cross section illustration of an exemplary bioreactor that can be used to culture plant cells.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention is directed, in one main aspect, to a three-dimensional (3D) bioreactor for cultivating proliferating plant cells comprising at least one packed bed chamber configured to confine said proliferating plant cells within it such that the proliferating plant cells become a three-dimensional stationary biomass phase; and at least one container comprising a fluid media, the fluid media is configured to flow through said proliferating plant cells stationary biomass phase; wherein, the flow of the fluid media through the proliferating plant cells stationary biomass phase allows transfer of compounds from the fluid media into the cells and vice versa in low shear forces within the at least one packed bed chamber thereby imitating natural growth environment of the proliferating plant cells within the 3D bioreactor.

The present invention is further directed to a method for cultivating proliferating plant cells in a 3D bioreactor comprising the steps of: a) confining proliferating plant cells within at least one packed bed chamber such that the proliferating plant cells become a stationary biomass phase; and b) flowing media through said proliferating plant cells stationary biomass phase, from at least one container comprising a fluid media; wherein, the flow of the fluid media through the proliferating plant cells stationary biomass phase allows transfer of compounds from the fluid media into the cells and vice versa in low shear forces within the at least one packed bed chamber thereby imitating natural growth environment of the proliferating plant cells within the 3D bioreactor.

Yet in a further aspect, the invention is directed to a method for cultivating proliferating plant cell for usage of the plant cells and/or compounds produced by said plant cells for medical, cosmetic, food tech, agriculture, and industrial applications using the bioreactor described herein, the method comprising: a) inputting proliferating plant cells onto at least one packed bed chamber in a bioreactor, wherein said packed bed chamber confines the proliferating plant cells within said packed bed chamber such that the proliferating plant cells create a stationary biomass phase; and b) flowing at least one fluid media from at least one container comprising a fluid media through the stationary biomass phase in a low-shear environment, allowing for efficient transfer of compounds between the fluid and the cells, wherein said fluid media contains one or more of nutrients, hormones, plant growth regulators (PGRs), vitamins, amino acids, trace elements, or combinations thereof.

The main aspects of this invention and optional ways to practice this invention will be better understood by the detailed description below of various exemplifying non-limiting drawings and examples described hereinbelow. Reference is now made to the drawings:

FIG. 1A is a schematic cross section illustration of an example of a bioreactor 400 that can be used to culture plant cells. The terms "plant cells", "plant cells culture", "plant cells aggregates", "plant cells callus", "callus" and "proliferating plant cells" are all directed to describe cells originated from plants and are used in the following text interchangeably. Callus is a pluripotent plant cell mass produced by a wounding signal or a hormonal treatment. Callus can be produced from a single differentiating plant cell, and plurality of callus cells (calli) are able to regenerate a whole plant body. As known in the art, calli produce a three-dimensional structure in three stages: induction, division and differentiation. These developmental stages may be characterized by changes in mean cell size as well as in the structure and overall metabolic condition of the plant tissue. In the division stage, which performs throughout the outer regions (periphery), callus cells size is decreasing while a small core of undivided cells is kept inside. These outer regions then differentiate and start maturation. The proliferating cells create a three-dimensional structure, in which each cell is growing in a 3D manner with respect to the adjacent cells, such that 3D cells aggregates are formed. The 3D cells aggregates create by themselves an independent biomass that may grow independently without carriers in contrast to animal cells (for additional detail, see: Fehér A (2019) Callus, Dedifferentiation, Totipotency, Somatic Embryogenesis: What These Terms Mean in the Era of Molecular Plant Biology? *Front. Plant Sci.* 10:536).

In the depicted embodiment, a growth and vibrating basket 416 (denoted hereinafter: "basket") is preferably but not necessarily, loaded with carriers such as, but not limited to, polyester disks 10. The terms "carrier/s" and "scaffold/s" may be used interchangeably and are both refer to elements configured to be added to basket 416 and to serve as a platform for the plant cells to be based onto them or within them and grow. The basket wall 4161 is preferably separated from the bioreactor inner wall 40 and can be moved upward and downward. In some embodiments, bioreactor 400 is filled with deionized water or isotonic buffer via an inlet pipe 420 that is configured and operable to deliver various media into the bioreactor, and then optionally be autoclaved. In other embodiments, following sterilization, the liquid is replaced with growth medium, which saturates basket 416 and its content. Basket 416 practically divides the fluids within bioreactor 400 into three main sections: upper section 422 that mainly comprises fresh media inserted via inlet pipe 420, middle section 424 that contains the media within basket 416 surrounding the plant cells and/or carriers, and lower section 426 that mainly comprises media that flowed through the plant cells, and compared to the fresh media at upper section 422 it is usually poor of nutrients that were consumed by the plant cells at the middle section, and rich with compounds and debris that are secreted by the plant cells. In the embodiment described herein, the media at the upper section 422 is being steered by impeller 419 that creates movement of the fluid as depicted by arrows 409. In still further embodiments, temperature, pH, dissolved oxygen concentration, etc., are set prior to inoculation and constantly adapted to the cultivation conditions as needed. In yet further embodiments, a slow initial stirring rate of the medium is used to promote cells attachment, then the stirring rate is increased. If desired, metabolic products may be harvested from the cell-free medium below the basket, during growth of the plant cells. In some embodiments, rotation of impeller 419 creates negative pressure in the draft-tube 450, which pulls cell-free media from lower section 426 through draft tube 450, then through impeller 419 ports into upper section 422, thus causing the medium to circulate in the direction according to arrows 409 uniformly in a continuous loop. In still further embodiments, adjustment of the media can be made by monitoring various parameters via electrode 406 so as to control the fluid various parameters. In some optional embodiments, a ring sparger (not visible), is located inside the impeller aeration chamber 11, for oxygenating the medium flowing through impeller 419 ports, via gases added from an external port 403, which may be kept inside a housing 5, and a sparger line 7. In some other optional embodiments, gases may be added through inlet 420. Alternatively, sparged gas may be confined to a remote chamber and be absorbed by the nutrient medium, which washes over the immobilized plant cells. In some optional embodiments, a water jacket 417 is coating media area within bioreactor 400, with ports for moving the jacket water in 13 and out 14. Removal pipe 410 is positioned along the bioreactor and has an opening within lower media section 426 to allow, if desired, to harvest metabolic products secreted by the plant cells from the cell-free medium below basket 416. Removal pipe 410 may also be used to collect the harvested cells, to remove debris, and for refreshing the media upon partial removal of the used media and addition of fresh media.

In some embodiments, a continuous stirred tank bioreactor may be used, where a culture medium is continuously fed into the bioreactor and a product is continuously drawn out, to maintain a time-constant steady state within the bioreactor. A stirred tank bioreactor with a fibrous bed basket is available for example from New Brunswick Scientific Co., Edison, NJ). Additional bioreactors that may be used, such as but not limited to, stationary-bed bioreactors, perfusion bioreactors with polyactive foams, radial-flow perfusion bioreactors containing tubular poly-L-lactic acid (PLLA) porous scaffolds and any other bioreactors known in the art that are suitable for the purposes of the present invention. A "stationary-bed bioreactor" refers to a bioreactor in which the cellular growth substrate is not ordinarily lifted from the bottom of the incubation vessel in the presence of growth medium. For example, the substrate may have sufficient density to prevent being lifted and/or it may be packed by mechanical pressure to prevent it from being lifted. The substrate may be either a single body or multiple bodies. Typically, the substrate remains substantially in place during the standard agitation rate of the bioreactor. In some embodiments, multiple carriers are loosely packed, for example forming a loose packed bed, which is submerged in a nutrient medium.

In certain embodiments, a perfused bioreactor is used, wherein the perfusion chamber contains a 3D substrate. In certain embodiments, the 3D substrate is in the form of carriers 10. The carriers may be, for example, macro carriers, microcarriers, or a mixture thereof. Non-limiting examples of microcarriers that are available commercially include alginate-based (GEM, Global Cell Solutions), dextran-based (Cytodex®, GE Healthcare), collagen-based (Cultispher®, Percell Biolytica), and polystyrene-based (SoloHill Engineering) microcarriers. In certain embodiments, the microcarriers are packed inside the perfused bioreactor.

In some embodiments, the carriers in the perfused bioreactor are packed, for example forming a packed bed, which is submerged in a nutrient medium. Alternatively or in addition, the carriers may comprise an adherent material. In other embodiments, the surface of the carriers comprises an adherent material, or the surface of the carriers is adherent. In still other embodiments, the material exhibits a chemical structure such as charged surface exposed groups, which allows cell adhesion. Optionally, the carriers may comprise a fibrous material, optionally an adherent, fibrous material, which may be, in more specific embodiments, a woven fibrous matrix, a non-woven fibrous matrix, or either. Carriers may be composed of natural occurring polymers, such as but not limited to proteins, alginate, cellulose, carbohydrates, silk, wool, natural rubber (latex), and others. Alternatively, fibrous carriers available in the market may also be used in accordance with optional embodiments of the present invention. In some embodiments, the media within the bioreactor do not contain any carriers and the plant cells, thanks to their inherited ability to grow as aggregates can grow within the growth basket as will be described in detail with reference to FIG. 5D hereinbelow.

In further embodiments, cells are seeded onto a scaffold by suspending them in medium and introducing the medium to the apparatus. In still further embodiments, the stirring speed is gradually increased, for example by starting at 40 RPM for 4 hours, then gradually increasing the speed to 400 RPM. In certain embodiments, the glucose or sucrose levels of the medium may be tested periodically, and the perfusion speed adjusted maintain an acceptable glucose/sucrose concentration, which is, in certain embodiments, between 5-30, 000 mg/l, between 5-1,000 mg/l, between 1,000-5,000 mg/l, between 1000-10,000 mg/l, between 5,000-10,000 mg/l, between 10,000-20,000 mg/l, between 15,000-25,000 mg/l. In yet other embodiments, at the end of the culture process, the carriers are removed from the packed bed and, in some embodiments, washed with isotonic buffer, and the cells are processed or removed from the carriers by agitation and/or enzymatic digestion.

In certain embodiments, the bioreactor is seeded at proliferating plant cells weight range of between 0.05-1.0 mg/ml, between 0.25-0.5 mg/ml, or between 0.5-1.0 mg/ml.

In still other embodiments, between 0.5-140 gram cells per gram (gr) of carrier (substrate) are seeded, or in other embodiments 0.5-2 gram cells/gr carrier, or in other embodiments 2-4 gram cells/gr carrier, or in other embodiments 4-8 gram cells/gr carrier, or in other embodiments 8-16 gram cells/gr carrier, or in other embodiments 16-32 gram cells/gr carrier, or in other embodiments 16-32 gram cells/gr carrier, or in other embodiments 32-48 gram cells/gr carrier, or in other embodiments 48-64 gram cells/gr carrier, or in other embodiments 64-80 gram cells/gr carrier, or in other embodiments 80-92 gram cells/gr carrier, or in other embodiments 92-104 gram cells/gr carrier, or in other embodiments 104-116 gram cells/gr carrier, or in other embodiments 116-128 gram cells/gr carrier, or in other embodiments 128-140 gram cells/gr carrier.

Figure 1B:
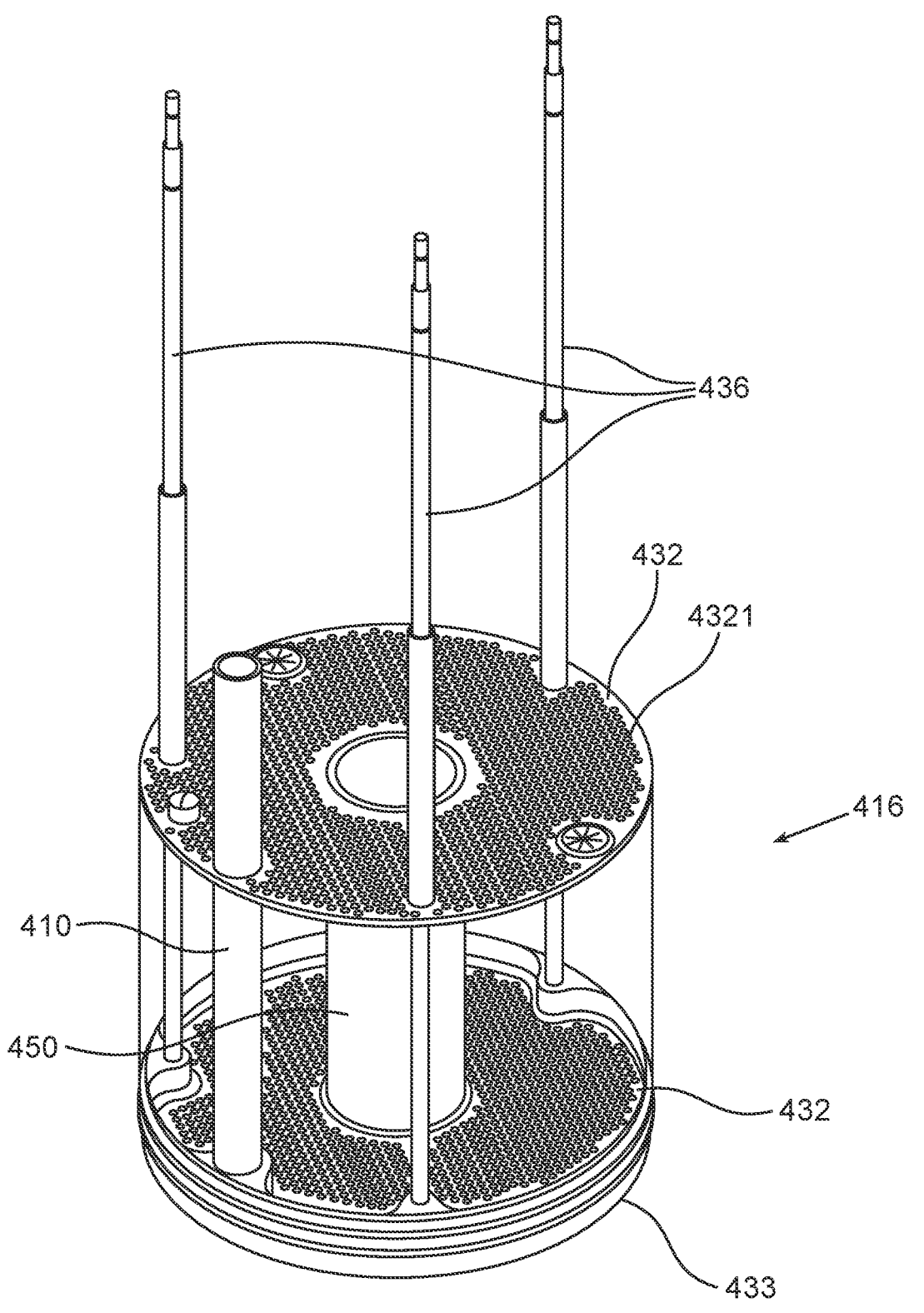
FIG. 1B is a schematic isometric top view illustration of an example of a growth and vibrating basket for plant cells.

FIG. 1B is a schematic isometric top view illustration of one optional example of growth and vibrating basket 416 for proliferating plant cells culturing in a packed bed bioreactor. The top and bottom borders of basket 416 are composed of perforated discs 432 each having a plurality of holes 4321 in a predefined diameter/s. Perforated disc 432 is also denoted hereinafter: "disc", "grid", "upper grid", lower grid", "middle grid" all can be used interchangeably and directed to the upper, middle or lower walls of basket 416. In some optional embodiments, when carriers are used, the carriers are "sitting" on the bottom grid and block the ability of the aggregates to come out from the other side, thus, the proliferating plant cells do not leave the basket from this direction. From the top side where they enter the basket, the flow in the basket is built in such a manner that it always flows inward, and therefore the plant cells aggregate that enters basket 416 cannot move against the current and will remain inside basket 416 (the cells are trapped within the basket and remain there).

In other optional embodiments, at the beginning of the culturing process of the proliferating plant cells within the bioreactor, the plant cells can pass through the disk holes as long as the proliferating plant cells aggregates are having dimensions smaller than the disk holes. Upon growth of the proliferating plant cell aggregates within the bioreactor, at a certain point of time the plant cell aggregates remain "trapped" within basket 416 and only the media keep flowing in between them, rinsing the plant cells aggregates. This is unique plant-specific character in contrast to animal cells that must be attached to carrier in order to stay within a growth basket and not circulate with the flow media. The inventors of the present invention found a method to cultivate plant cells with or without using carriers within the packed bed chamber, as long as the stationary biomass of the proliferating plant cells is obtained within the packed bed chamber.

At the center of basket 416 the impeller draft tube 450 is shown, and removal pipe 410 is also shown, crossing both upper and lower discs 432 in order to reach lower media section (not shown) and allow collection of the media if desired to harvest metabolic products secreted by the plant cells from lower media section 426. Basket 416 is preferably connected to one or more vibrating rods 436 configured to allow vertical vibrating of basket 416. When performed in low intensity, the vertical vibrating of basket 416 can be used to avoid channeling effect, thereby, it enables to maintain homogeneous distribution of media within the basket and thus, homogeneous growth for a longer period, and further to release clogging. When vibration is performed in medium intensity it can be used for releasing the proliferating plant cells stationary biomass from basket 416, and when the vertical vibration is held in high intensity, it can be used for separating the cells aggregates for collection of the cells, and for cells lysis and collection of metabolites from the harvested cultivated proliferating plant cells stationary biomass. For that purpose, combining enzymatic reaction together with the strong vibration force may be applied.

Also shown in this drawing, gasket 433 that is configured to prevent the movement of the plant cells outside and around of culturing basket 416 into lower section 426 of bioreactor 400 during the growth stage. Cells aggregates may be collected directly from basket 416.

Figure 2:
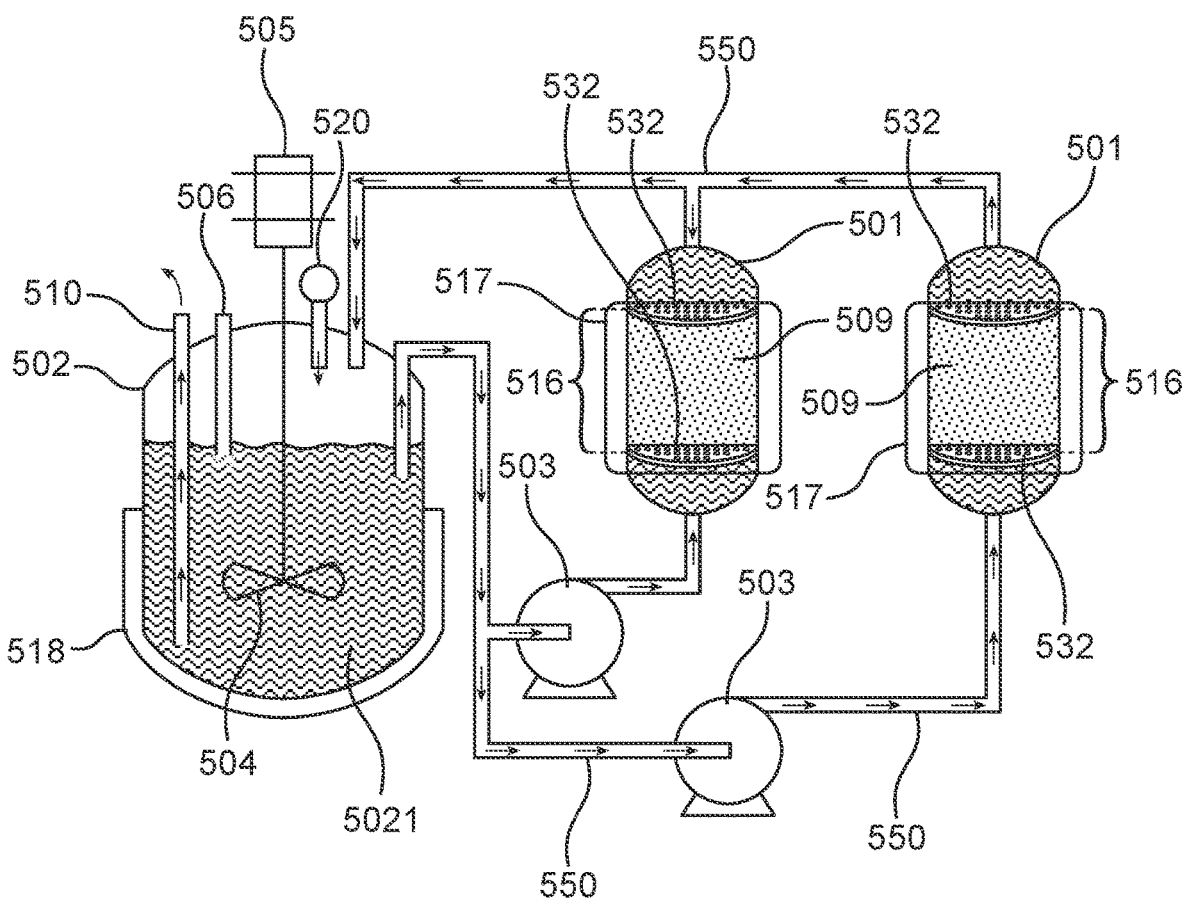
FIG. 2 is a schematic illustration of an exemplary embodiment of a modular bioreactor for proliferating plant cells growth.

FIG. 2 is a schematic illustration of an exemplary embodiment of a modular bioreactor 500 for proliferating plant cells culturing, in accordance with some optional embodiments of the present invention. In the example illustrated herein, modular bioreactor 500 comprises a central medium container (reservoir) 502, comprising a cell culture medium 5021, wherein central medium container 502 does not contain plant cells; and one or more 3D proliferating plant cells growth vessels 501. Each of the proliferating plant cells growth vessels 501 may comprise microcarriers composed of a 3D substrate 509 (such as but not limited to a fibrous matrix), which may be made of a synthetic matrix or natural matrix. The central medium container 502 is operably connected to each proliferating plant cells growth vessels 501 via tubing 550, such that the medium from the medium container 502 flows through vessels 501 in parallel or successively, and in some embodiment through carriers or microcarriers, if used. In certain embodiments, the flow may be against gravity. More specifically, vessels may be oriented vertically, with the flow in an upward direction. In other embodiments, a plurality of plant cells carriers (not depicted) composed of 3D substrate 509 are disposed within each of proliferating plant cells vessels 501. Optionally, the modular bioreactor 500 is aseptically sealed. In other embodiments, the described bioreactor is a closed system. The rational of using one or more proliferating plant cells culturing vessels 501 simultaneously is to increase the growth production abilities of modular bioreactor 500 and thus, to increase the size of the batch. By using separated, several subunits for growing the proliferating plant cells a scaleup of the growth process is achieved without facing the challenges that usually occur due to scaling up and may affect the growth of the proliferating plant cells. Cultivating proliferating plant cells in a bioreactor may have certain limitations related to scaling up that may damage the culturing process. By dividing the plant cells culturing vessels into plurality of vessels that are all connected to each other, we scale up the process without suffering the damage that may occur when scaling up the process in one large container.

Optionally, modular bioreactor 500 further comprises one or more circulation pumps 503 or other means for actively transporting the medium through the proliferating plant cells vessels 501. In certain embodiments, each proliferating plant cells vessel 501 is connected to dedicated pump 503.

In yet other embodiments, each of the plurality of vessels 501 is temperature-insulated. Additionally or alternatively, central medium container 502 is temperature-insulated. Non-limiting examples of temperature insulation are medium container water jacket 518 and vessel water jacket 517, which may be independently various types of water jackets known in the art. In still other embodiments, both central medium container 502 and plant cells growth vessels 501 are temperature controlled, or, in other embodiments, are operably connected with a thermostat and/or thermometer and/or other mean for monitoring and controlling the temperatures of the fluid contents thereof.

The term "3D proliferating plant cells growth vessel(s)", as used herein, refers to a vessel (e.g. as depicted in 501) configured to hold proliferating plant cell stationary biomass with a fluid medium and flowing through the proliferating plant cells stationary biomass, wherein the proliferating plant cells may grow on carriers 509 or without carriers. Thus, in certain embodiments, the proliferating plant cells in the described vessels grows as callus that creates stationary biomass by themselves, and in certain other embodiments, the plant cells are adhered to the carriers during cultivation as described in FIGS. 5A-5D. The carriers may be, in more specific embodiments, selected from macro carriers, micro-carriers, or both. Non-limiting examples of microcarriers that are available commercially include alginate-based (GEM, Global Cell Solutions), dextran-based (Cytodex, GE Healthcare), collagen-based (Cultispher, Percell), and poly-styrene-based (SoloHill Engineering) microcarriers. In certain embodiments, the microcarriers are packed inside the vessels. In other embodiments, the carriers are fibrous 3D carriers that comprise an adherent material.

Medium container 502 may contain a stirring element, such as impeller 504, which is driven by motor 505 so as to mix the medium 5021 within medium container 502. Those skilled in the art will appreciate, in light of the present disclosure, that other suitable mixing devices may be used such as, but not limited to, marine-blade impellers, pitched-bladed impellers, hydrofoil impellers, Rushton impellers, pitched-blade impellers, CelliGen® cell-lift impeller, A320 Impeller (SPX Flow), HE3 Impeller (Chemineer), and else.

Optionally, medium container 502 may be connected with one or more control element 506, for monitoring and controlling various parameters including pH rate, dissolved oxygen concentration, and temperature. Other parameters that follow-up cell proliferation, culture uptake rates and status and media osmolarity, may also be monitored. In some optional embodiments, minerals and compounds concentration, that affect cells growth for instance, phosphate, ammonia, glucose, and sucrose may be monitored. Optionally, optical density (OD) of the medium, which indicates cell adherence to the carriers within the growth vessel 501 may also be monitored. Feed line 520 for introducing fresh medium to the medium container 502, and waste line 510 for removing medium that was circulated through the proliferating plant cells from medium container 502. Preferably, perfusion involves the functions of both feed line 520 and waste line 510. Control element 506 may include a pH adjustment solution line (not depicted), for adding basic or acidic solution, as necessary to modulate the pH. Perforated disks 532 define the top and bottom borders of growth basket 516 and configured to confine the proliferated plant cells aggregates to grow within growth basket 516 and prevent them from circulating together with the media via tubes 550.

Figures 3A, 3B:
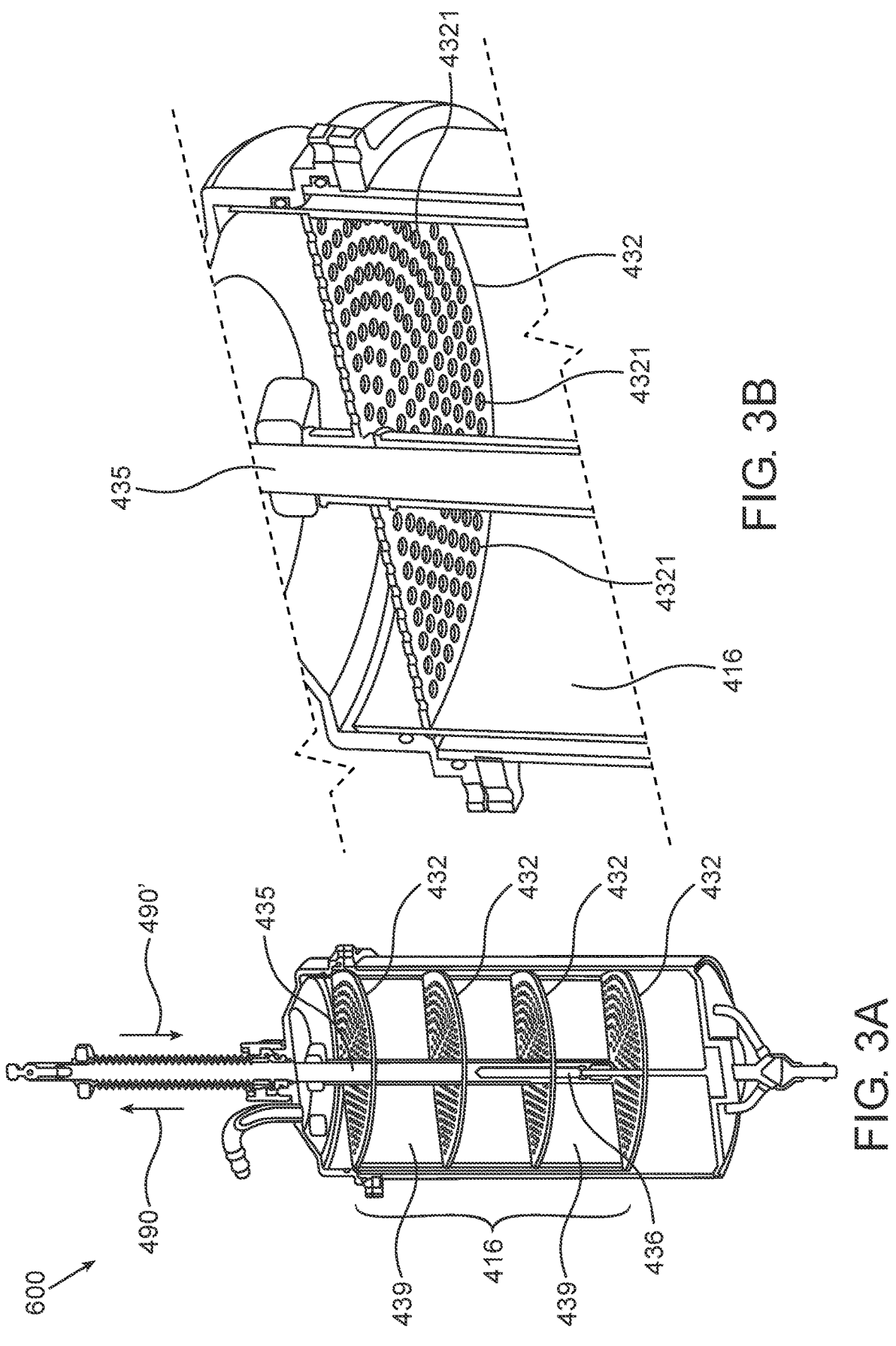
FIG. 3A is a schematic isometric cross section front view of an exemplary plant cells vessel.
FIG. 3B is a schematic close up isometric bottom view of the upper perforated disk of the plant cells vessel of FIG. 3A.

FIG. 3A is a schematic isometric cross section front view illustration of one another exemplary plant cells bioreactor 600 that is similar to bioreactor 400 illustrated in FIG. 1A but having a cell basket 416 divided into at least one more sub chamber 439 by additional perforated disks 432 positioned along the longitudinal axis of basket 416. In the specific example illustrated in this drawing, cell plant basket 416 is divided in total to three sub-chambers by addition of two more perforated disks 432 between the upper and bottom perforated disks, which define the upper and bottom borders of the cell basket. The size of the holes in each one of the perforated disks 432 may be the same, or it may vary between them, for example, the diameter of the holes may decrease from bottom to top, so as to create a gradient of callus sizes within the sub growth chambers 439, such that the upper cell chamber will contain the smallest proliferating plant cells, while the bottom cell chamber will contain the largest. Other optional variations may be applied. As mentioned above, culturing plant cell basket 416 may hold carriers also denoted hereafter: "scaffolds", both terms having the same meaning in accordance with the present invention and may be used interchangeably. Scaffolds are aimed to provide the proliferating plant cells with a growth platform. In some other embodiments, culturing plant cell basket 416 does not contain any carriers, thus allowing the proliferating plant cells to grow independently. The usage of carriers may vary in accordance with the plant cell type, the compounds of interest, and the specific growth protocol. When carriers are used, culturing cell basket 416 may be fully filled with carriers or partially filled with carriers.

Plant cell bioreactor 600 may further include basket positioning pin 436, which may mate with hollow longitudinal central axis 435 (denoted hereinafter: "longitudinal axis") of basket 416.

Growth basket 416 may have various dimensions and volumes. In certain dimensions, dividing the basket into several sub chambers allows to vibrate the cells within the basket more efficiently as perforated disks 432 transfer the vibrating forces in a vertical manner, upward and downward, as shown by arrows 490 and 490' respectively, more effectively to each adjacent proliferating cells. As mentioned above, vibrating the basket in low intensity is effective to avoid channeling effect and improve the flow of the growth media (or any other media that may be used) through the proliferating plant cells stationary biomass that is being cultured within growth basket 416, and to insure maximal contact between the proliferating plant cells and the flowing media. In addition, when the vibration is strong, the vibrating power can be used to break the cells and harvest their content. For harvest, basket 416 may be oscillated within (and relative to) bioreactor 600, along longitudinal axis 435 upward 490 and downward 490'.

Plant cells can be propagated, in some embodiments, by using a combination of suspension and 3D substrates, e.g., prior to and in conjunction with the disclosed modular bioreactor, respectively; using suitable growth medium/media known in the art. The term "medium", except were indicated otherwise, refers to a liquid composition designed for ex-vivo replication of proliferating plant cells. Further, non-limiting examples of suitable media are mentioned herein. The terms "growth" and/or "cultivation" of a population of proliferating plant cells is intended to be synonymous with expansion of proliferating plant cells population. In various embodiments, the described expansion may be in a suspension, followed by a 3D substrate.

In other embodiments, there is provided a method for culturing proliferating plant cells, comprising expanding cells in the described apparatus. In certain embodiments, culturing in the described apparatus is preceded by suspension culturing. Any described embodiments of the apparatus may be applied to the culturing methods.

In certain embodiments, the bioreactors systems for plant cells culturing described herein are closed systems. Alternatively or in addition, the described processes are automated processes, at least partially. Those skilled in the art will appreciate in light of the present disclosure that closed systems are sealed from the outside environment, in a manner enabling maintenance of sterility. In further embodiments, closed systems are sealed in a manner preventing unintentional contamination by substances outside the system. In yet other embodiments, closed systems are sealed in an airtight manner. The skilled person will further appreciate that closed systems enable manipulation of the contents thereof without requiring the manipulation to take place inside a sterile hood or sterile room.

In some optional embodiments, any of the described methods further comprises determining the concentration of the plant cells aggregates in the growth vessels/basket. Thus, the described growth vessels/plant cells basket is/are optionally further operably connected to a sensor for determining the cell concentration.

In still other embodiments, any of the described methods further comprises measuring viability of cells in the growth vessels/basket. In other embodiments, the described apparatus further comprises a probe, or other means for measuring viability of cells in the growth vessels.

In yet other embodiments, any of the described methods further comprises monitoring and/or controlling pH of the medium in central medium container. Those skilled in the art will appreciate, in light of the present disclosure, that the pH of a liquid formulation can be adjusted in a variety of ways known in the art, non-limiting examples of which are addition of carbon dioxide ($CO_2$), base solution, acid solution, and/or pH buffer to the formulation. Non-limiting examples of means for adjusting pH include input channels and pumps for addition of $CO_2$, base solution, acid solution, and/or pH buffer to the formulation. In certain embodiments, the described system comprises adjustable controls for the pH of the formulation.

In other embodiments, any of the described methods further comprises monitoring and/or controlling the dissolved oxygen concentration ($pO_2$) inside the medium container, or in other embodiments, the growth vessels, or in other embodiments, both the medium container and the vessels. In other embodiments, the apparatus may further comprise a meter or other means of monitoring and/or controlling the dissolved oxygen concentration inside medium container, $pO_2$ can be adjusted (as a non-limiting example) by addition of $O_2$ to a formulation, in some embodiments using a pump. In certain embodiments, the described system comprises adjustable controls for the $pO_2$ of the medium inside the medium container. In still other embodiments, measurement of $pO_2$ serves to estimate the number of viable cells in the vessels.

In other embodiments, any of the described methods further comprises monitoring and/or controlling the temperature of the medium inside the medium container, or in other embodiments, the vessels, or in other embodiments, both the medium container and the vessels. Thus, the apparatus may further comprise a thermometer, thermostat, or other means of monitoring and/or controlling the temperature medium inside the medium container and/or the growth vessels, non-limiting examples of which are thermometers, insulation, and external containers for a fluid, e.g., a liquid or a gas, whose temperature can be manipulated. Methods for determining and adjusting temperature of a medium are well known in the art. In certain embodiments, the described system comprises adjustable controls for the temperature of the medium.

In yet other embodiments, any of the described methods further comprises collecting and/or storing data on conditions inside the medium container, which may be, e.g., glucose concentration, temperature, pH, dissolved oxygen concentration, etc. In other embodiments, the apparatus optionally further comprises a meter(s), connection to an external computer, and/or other means of collecting and/or storing data on conditions inside the medium container. In certain embodiments, the data is used to generate a report.

In still other embodiments, any of the described methods further comprises collecting and/or storing data on transfer of fluid into and/or out of the medium container, or in other embodiments, into or out of the vessels, or in still other embodiments, both the medium container and the vessels. In other embodiments, the apparatus optionally further comprises a meter(s), connection to an external computer, and/or other means of collecting and/or storing data on transfer of fluid into and/or out of the medium container and/or the vessels. In certain embodiments, the data is used to generate a report.

In yet other embodiments, any of the described methods further comprises controlling the flow rate of medium transferred into and/or out of the central medium container, or in other embodiments, into and/or out of the plant culturing vessels, or in still other embodiments, both the medium container and the vessels. In other embodiments, the apparatus optionally further comprises a meter(s), connection to an external computer, and/or other means of controlling a flow rate of medium transferred into, and/or out of, each of the culture vessels.

In yet other embodiments, any of the described methods further comprises facilitating uniform mixing of liquid contents of the described medium container when a stirrer/agitation device is activated (e.g., rotated). Thus, the medium container optionally further comprises one or more baffles that jut(s) inward from an inward surface of the container.

In still other embodiments, the described medium container is, optionally, further operably connected to an automatic calibrator and/or other means of calibrating other components and/or sensors described herein and/or monitoring the failure of one, some, or all of these components, of which represents a separate embodiment.

Each of the described optional method steps and optional components represents a separate embodiment, and they may be freely combined, in various embodiments.

Those skilled in the art will appreciate that, while three growth sub-chambers 439 are depicted in this drawing, use of different numbers and configurations of growth sub-chambers is consistent with the present disclosure. Each growth sub-chamber may have a similar or different volume compared to the other sub-chambers.

FIG. 3B is a schematic close up cross section isometric bottom view of upper perforated disk 432 of growth basket 416 of FIG. 3A. Shown in this view are holes 4321 all in a fixed diameter in a predetermined position on top of the disk such that they functionally create a physical barrier that allows media to flow through them but keep the plant cells aggregates within the basket. When carriers are used, they physically block the passage of the cells through the lower perforated disk when the cells aggregates are small, and then, the cell aggregates grow to dimensions that are larger than the diameter of holes 4321 and cannot pass through them. The size and distribution of the holes on the disk allows the turbulent flow from the impeller to be evenly and laminarly distributed at the entrance into basket 416. Additionally, the more evenly distributed holes there are, the more uniform material is transferred to all parts of the basket, thus allowing the basket to be enlarged to diameter. Also shown in this view is hollow longitudinal central axis 435.

Figures 4A, 4B:
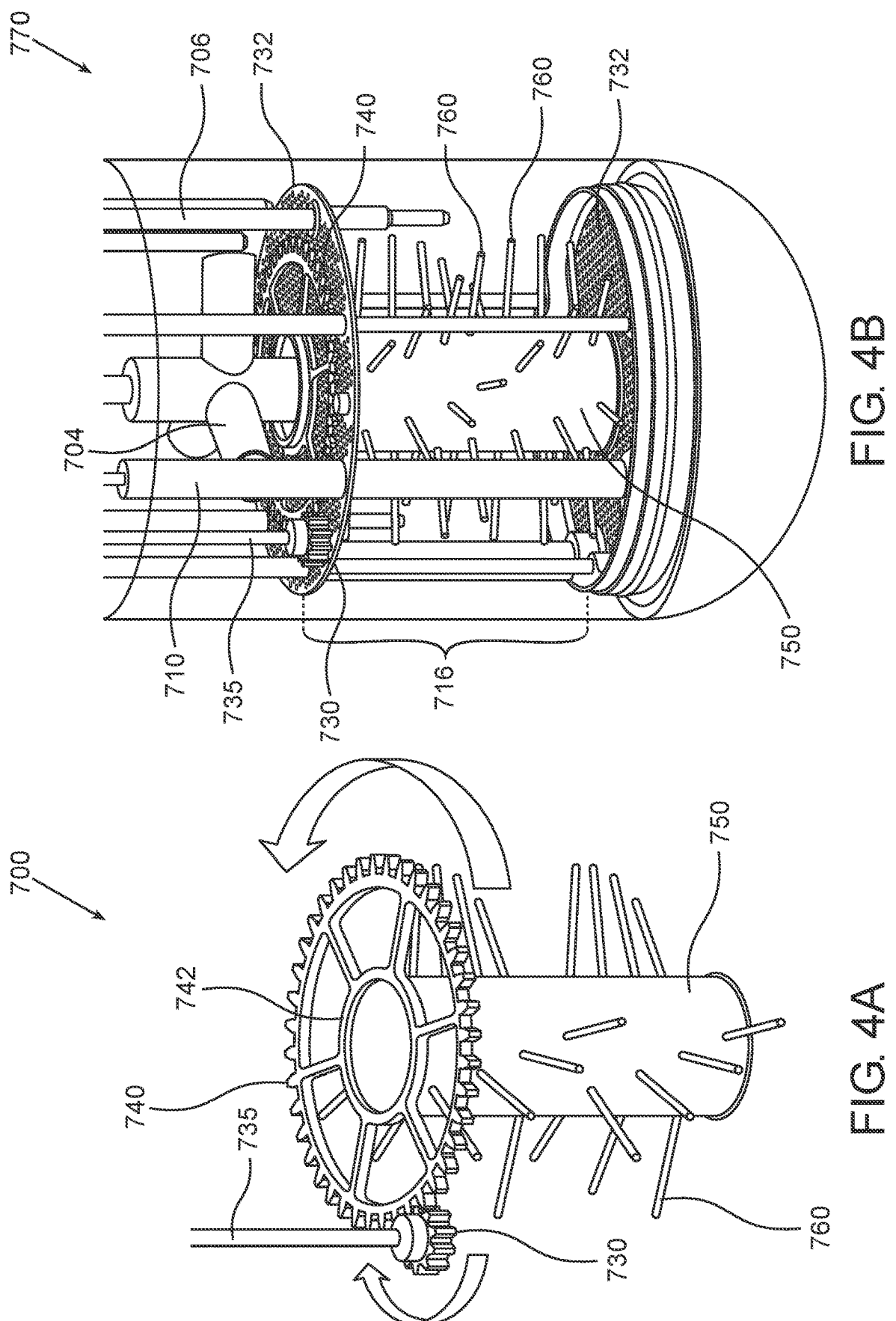
FIG. 4A is a schematic illustration of an exemplary stirring mechanism for stirring plant cells aggregates within a plant growth basket.
FIG. 4B is a schematic illustration of the stirring mechanism of FIG. 4A assembled on a packed bed bioreactor cell growth basket in accordance with embodiments of the invention.

FIG. 4A-4B are schematic isometric illustrations of an exemplary stirring mechanism 700 for stirring plant cells aggregates within a plant growth basket in a packed bed bioreactor; and a schematic front view illustration of the stirring mechanism 700 embedded within a growth basket 716 of a packed bed bioreactor 770, respectively.

The stirring mechanism 700 comprises a rotating cylinder 750, typically positioned along the central axis of packed bed bioreactor 770. Spokes 760 extend radially from rotating cylinder 750 inside growth basket area 716, imparting motion to the basket content when rotating cylinder 750 is rotated. Rotating cylinder 750 may be operably connected with an external component capable of transmitting applied torque that may optionally be either manually rotatable or connected with a motor (not shown) through handle 735. In the example illustrated in these figures, stirring mechanism 700 comprises a gear mechanism, including a small gear 730 attached to handle 735 that is extended outside growth basket 716 and can be spined either manually or by a motor, and a large gear 740 attached to an impeller 704. Large gear 740 is connected to rotating cylinder 750 trough ring 742 that is mounted on top of rotating cylinder 750 and rotate it together with it. Rotating cylinder 750 imparts a rotary motion to spokes 760 to thereby stir the content of growth basket 716, minimize the channeling effect and improve the contact area between the growth medium (or any other medium in use) and the plant cells within basket 716. In addition, stirring mechanism 700 can also be used to improve harvesting of the cells. Rotating cylinder 750 may rotate either in continuous rotary motion, or in other embodiments in a partial rotary motion, for example an oscillating partial rotary motion. It can rotate clockwise and counterclockwise, all according to the needs and design of the operator.

In still other embodiments the rotating cylinder 750 is operably connected to growth basket 716 in a manner that enables rotation of the basket itself relative to the outer chamber wall of bioreactor 770. Impeller 704 is also presented in FIG. 4B, in accordance with some optional embodiments of the invention, impeller 704 may be a cell-lift impeller, creating a vacuum pull from below, thus leading to downward fluid flow within cell basket 716. Cell-lift impeller 704 preferably rotates around the same axis as rotating cylinder 750 but is not operably connected with rotating cylinder 750. The term "cell-lift" impeller as used herein refers to an impeller having a vertical tube, whose rotating motion creates a low-differential pressure at the base of the tube. It should be clear that other types of impellers may also be used to practice the present invention.

Additional components such as removal pipe 710 (outlet port) is positioned along the bioreactor and allows, if desired, to collect metabolic products secreted by the plant cells from the cell-free medium below basket 716, electrode 706 that allows to monitor and control the various parameters of the culturing process and medium, and upper and lower perforated discs 732 that define the upper and lower borders of plant cells culturing basket 716 and allows to obtain and hold the plant cells from flowing with the media and become a stationary biomass phase.

FIGS. 5A-5E are schematic illustrations and pictures of various plant cells aggregates in different growth stages, growing with or without carriers within packed bed bioreactors.

Figure 5A:
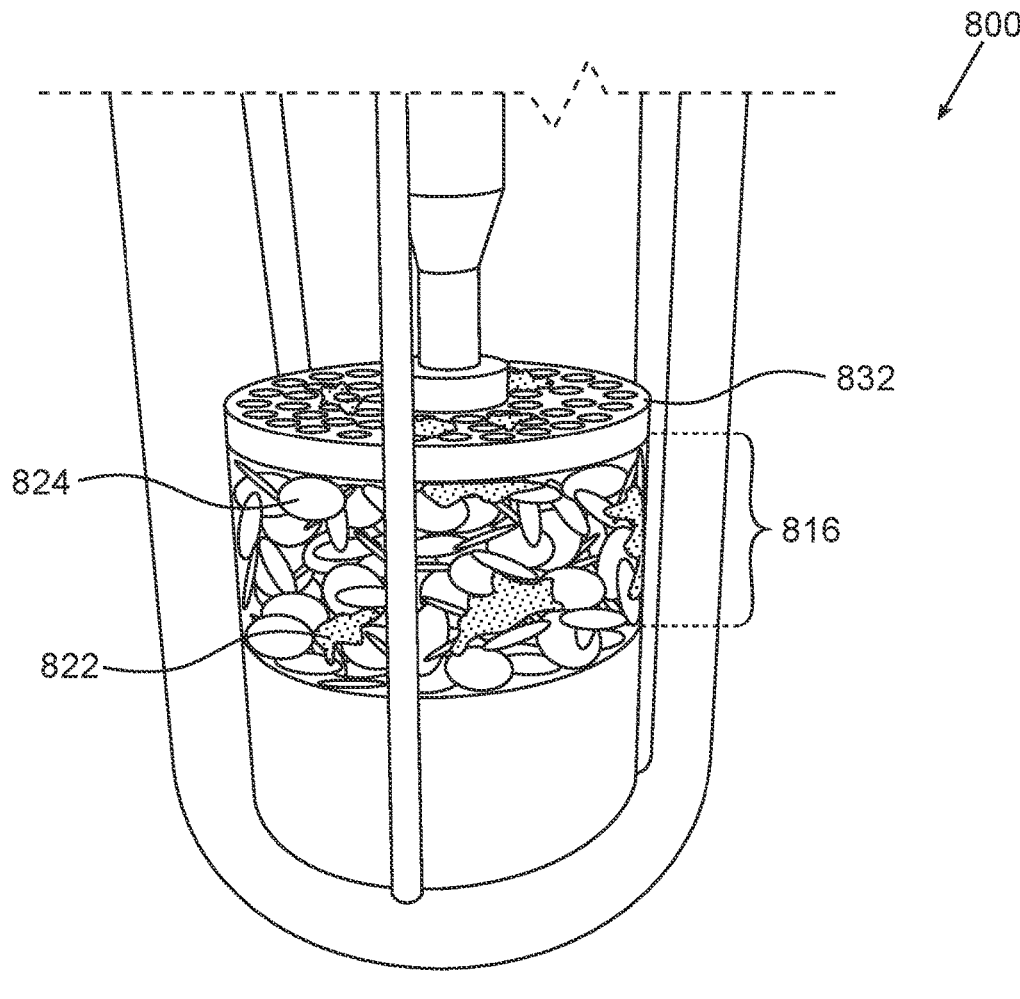
FIGS. 5A-5E are schematic illustrations and pictures of various plant cells aggregates in different growth stages, growing with or without carriers within packed bed bioreactors.

FIG. 5A is a schematic partial view illustration of a 3D mini packed bed bioreactor 800 illustrating the growth of plant cell aggregates 822 on top of scaffolds 824 within a growing basked 816. The plant cells aggregate are filling the growing basket and remain within the basked thanks to the upper and bottom perforated disks 832 that mechanically limit their ability to exit from the basket into the medium on top or below basket 816.

Figure 5B:
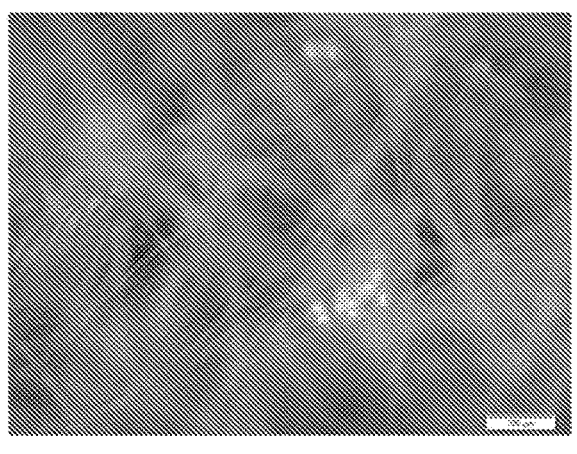
Figure 5C:
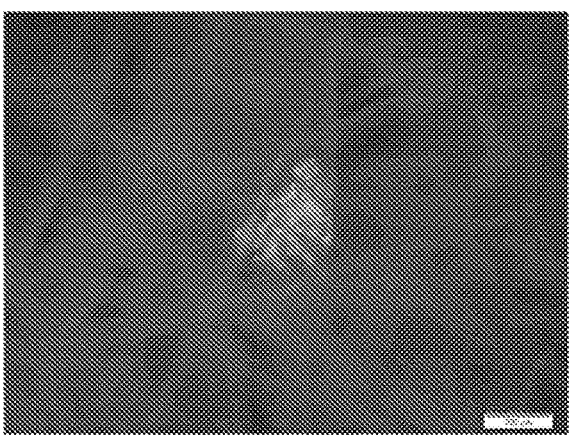

FIGS. 5B and 5C are pictorial illustrations of *Cannabis indica* plant cells expansion within 3D Fibracell™ carriers. The plant cells were cultured for a period of 21 days in a packed bed bioreactor. This resulted in the expansion of cell aggregates as shown in these drawings. The 3D carriers were stained with a specific DNA maker Hoechst. Cell aggregates are observed intercalated in carriers' fibers. Scale 100 μm.

Figure 5D:
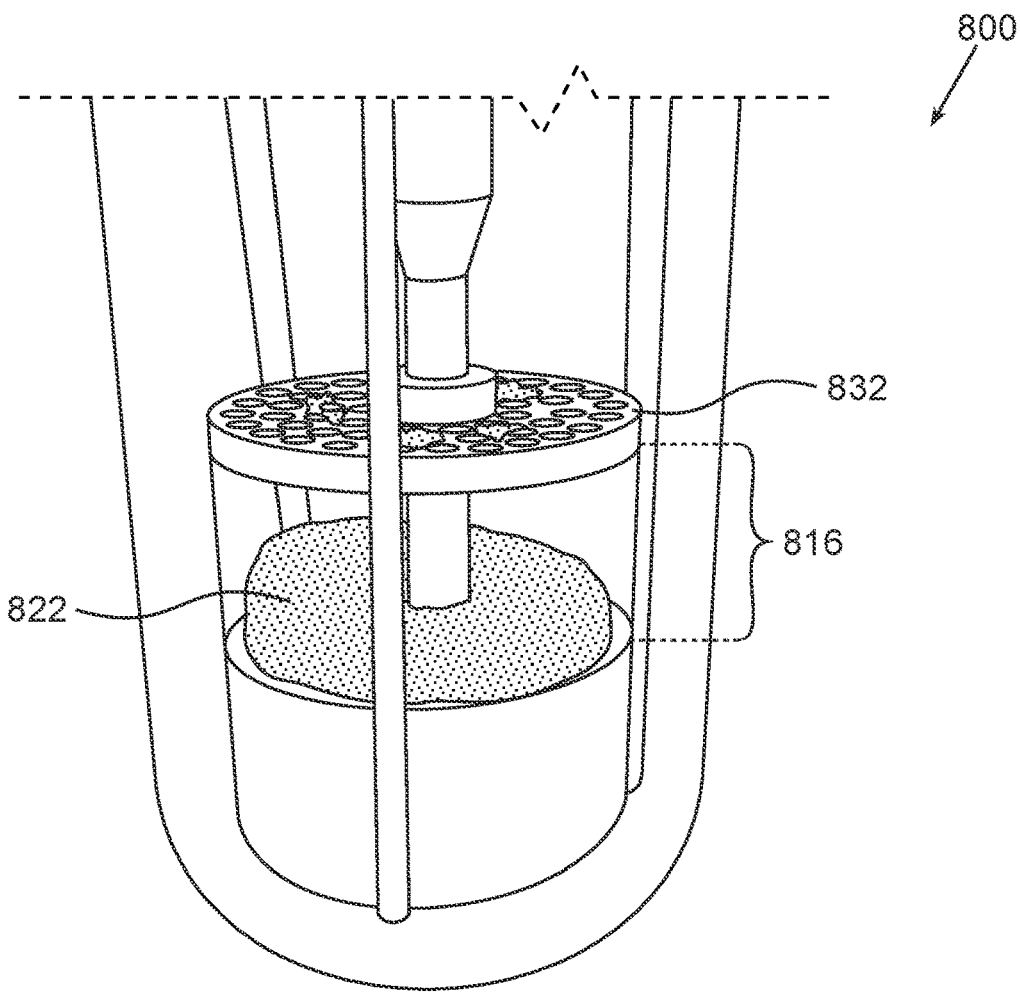

FIG. 5D schematically illustrates plant cells seeding and growth in a 3D mini bio system without carriers. Following the cultivation of *cannabis* cells in a 3D Mini-bio reactor. Although no carriers were used in the cultivation process after three weeks of cultivation, average cell aggregates diameter was increased by approximately 10 folds, which indicates cell culture proliferation.

Figure 5E:
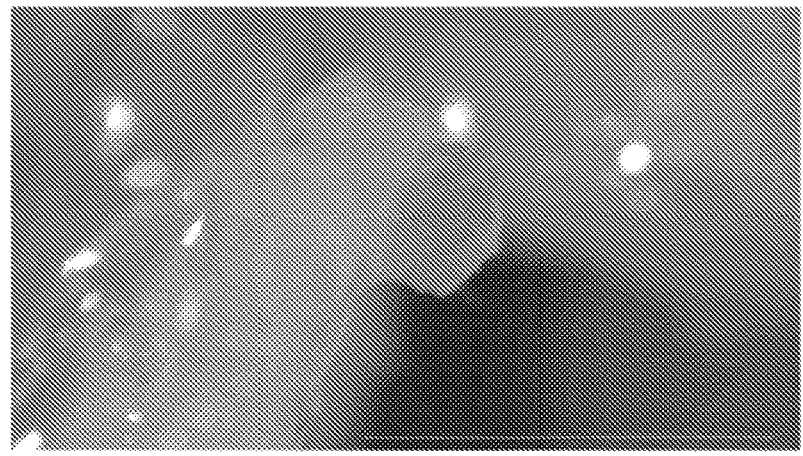

FIG. 5E is a pictorial illustrations of *Cannabis indica* plant cell aggregates adherence to Fibracell™ carriers. Culturing of the plant cells for a period of 21 days in a packed bed bioreactor resulted in cell aggregate adherence to 3D carriers. Proliferation of cell aggregates is shown since cell culture were strained to reach 300 μm at seeding and final aggregate size measured was above 500 μm. Scale 530 μm.

Figure 6A:
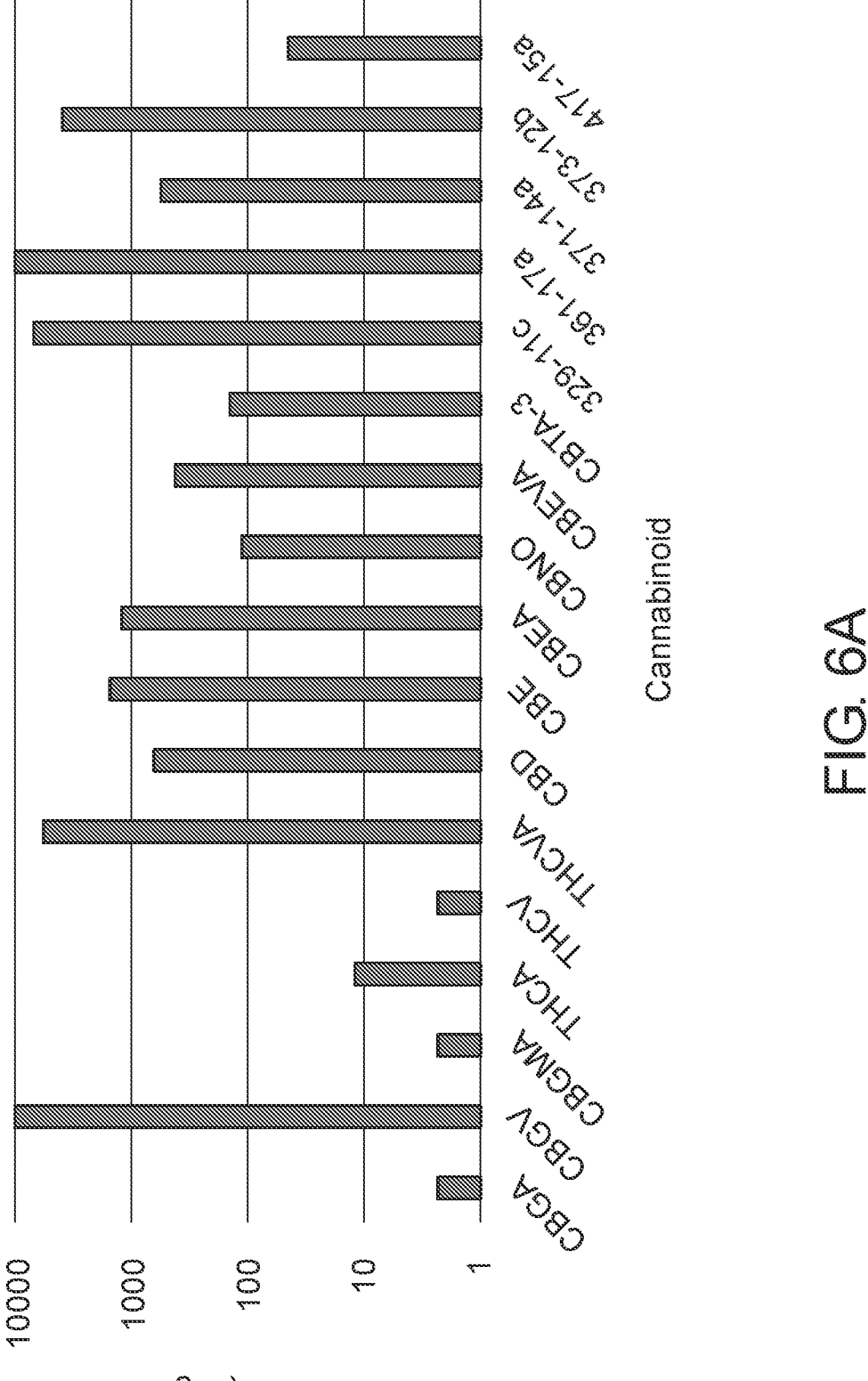
FIG. 6A is a chart illustrating Cannabinoids production ratio in a packed bed bioreactor relative to suspension cultures.

FIG. 6A is a chart illustrating Cannabinoids production ratio in a packed bed bioreactor relative to suspension cultures. As shown in this chart, there is a significant increase in the cannabinoid concentration in 3D bioreactor relative to suspension cultures. This increase reaches above 1000 fold increase in 3D bioreactor systems.

Figure 6B:
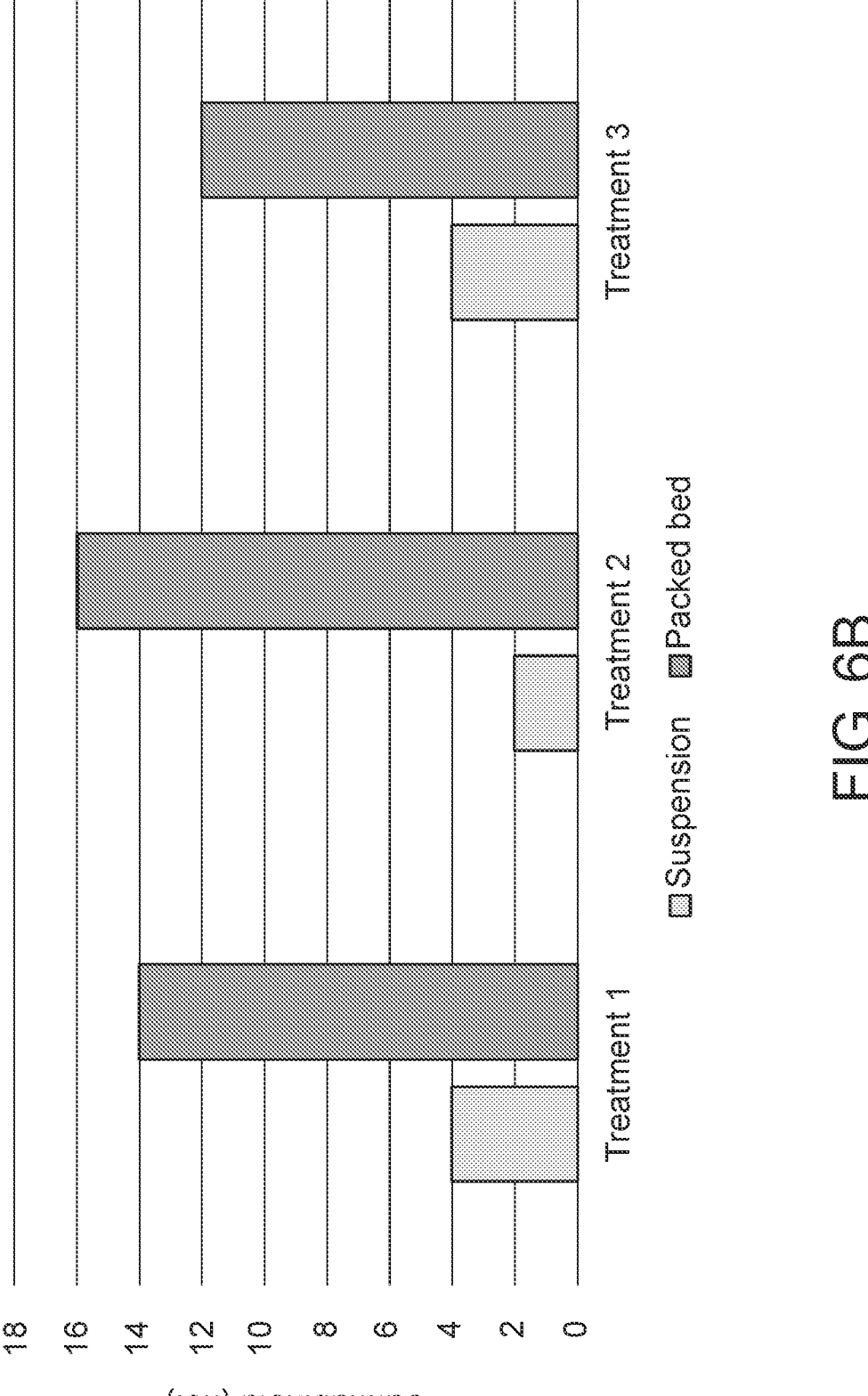
FIG. 6B. is a schematic chart demonstrating the amount of cannabinoid achieved in a packed bed bioreactor compared to the amount of cannabinoid achieved when the plant cells were cultivated in suspension cultures shake flasks.

FIG. 6B, is a schematic chart demonstrating the amount of cannabinoid achieved when the plant cells were cultivated in a packed bed bioreactor of the present invention, compared to the amount of cannabinoid achieved when plant cells were cultivated in suspension cultures shake flasks, where all other conditions were similar. These results demonstrate the 3D system ability to induce and significantly increase the cell culture cannabinoids production potential.

This potential is manifested in the number of cannabinoids produced under suspension and 3D system, which shows a maximal 8 folds increase in cannabinoids in the 3D system. Biomass yield, metabolite content and profile results indicate higher biomass and cannabinoids yield, both in total amount and profile, in packed bed bioreactors.

EXAMPLES

Generic Plant Cell Culture Process Workflow in a 3D Packed Bed Bioreactor

Following the cultivation of cell cultures in 2D and suspension methods, cultures are treated to reach final product specification and to increase production yield via 3D system.

The following steps are a general description of the process and are relevant for various plants and products lines.

Step 1. 3D Pre-Seeding Procedures

Following the cell isolation and cultivation of specific tissue derived cells the cell culture for 3D seeding in 3D system was prepared. The goal was to reach the desires aggregate size to fit the mini-bio systems. This was conducted both to reach cell culture uniformity and to enable the physical procedure of seeding through low diameter tubing. During that process the inventors examined the aggregate size (0-700 μm) and the seeding procedure technical details such as cell biomass concentration, flow rates, time, and RPM throughout the process.

Certain parameters were examined to make sure that the seeding procedure was conducted as planned.

Step 2. Cell Growth for Biomass Accumulation

In this stage a specific medium is used to increase biomass accumulation and to initiate the differentiation of the cell culture to be able to produce desired secondary metabolites and/or active compounds. For example, when the aim is production of Cannabinoids, the media provided to the cell culture shell contain specific cannabinoids precursors, such as olivetolic acid. The time period for this stage may range between 10-28 days, depending on the action required and the plant strain. The action may be to produce full or vast cannabinoid profile, or it may be specific cannabinoids such as one or more minor cannabinoids.

In this step the aim is to allow the cell expansion to reach the highest biomass of cell culture. During this stage the medium uptake is monitored, and replenished via perfusion, if required. Once the biomass accumulation is reached the next step of cell differentiation and/or metabolite production may begin.

Step 3. Cell Culture Manipulation

During this stage, the inventors "drive" the cell culture to produce and/or to reach the product manufacturing process. This stage characteristic is highly dependent on the final product, and it may include cell culture maturation, differentiation and metabolite production via elicitation. For *Cannabis*, for example, elicitation is used for a period of 1-16 days for activating the cell culture to produce the desired product. Since secondary metabolites in plants function as protection compounds, a stress condition (biotic/abiotic) was created to induce a stress response for activating the cell culture to produce its "defending" metabolites. Manipulation via media content that activates cell differentiation and maturation may be adapted to the specific plant species and the metabolite of interest.

Step 4. Final Product Manufacturing

During this stage further production of certain metabolites may be induced, the growth media may be changed to allow long term stability of the desired product or for changing specific characteristics in the final product. For example, to wash the cell culture with a control feeding media when accumulation of metabolite production is observed in the cell culture and in the growth media. Optionally, during steps 3 and 4 the media can be collected since the media consists of specific desired metabolites such as cannabinoids, caffeine, vanillin and the like, according to the plant cells cultured and the culturing conditions.

The above general workflow will be better understood by the following detailed examples.

Example 1: *Cannabis* Plant Cell Seeding to a Packed Bed Bioreactor

*Cannabis indica* callus cell cultures derived from sterile internode tissues were maintained in liquid MS medium (Duchefa cat. M0221) containing essential vitamins (Gamborg Bs), sugars and phytohormones. Following sufficient biomass accumulation, cultures aggregate size was selected for seeding using a 1 mm strainer. Cell culture was poured into a 1 mm strainer positioned on a beaker and washed thoroughly. Hence, the beaker contained cells having a diameter lower than 1 mm. The cells were collected and used as an initial inoculum for bioreactor seeding. In addition, the bioreactor head plate was modified such that the tubing inner diameter increased to prevent clogging of pipeline. The minimal inner diameter of the tubing that was used was 6 mm long. Wet weight of 8.5 g of *Cannabis indica* cell cultures were seeded at 200 rpm for a period of five (5) hours, or until the Optical Density (OD) of the growth media was similar to a blank medium measurement (See table 1 below). OD measurement supported visual inspection of medium turbidity and cell content, as can be observed in FIG. 5A. Cultivation of cell cultures was conducted in 350 ml packed bed modified AppliKon™ bioreactor. OD measurements data presented in Table 1 below.

TABLE 1

| Optical Density measurements during cell culture seeding packed bed bioreactor. | | |
|---|---|---|
| | Optical density (595 nm) | Calculated OD |
| Medium without cells | 0.071 | 0 |
| seeding vessel pre seeding | 0.104 | 0.033 |
| System post seeding (t = 0) | 0.0885 | 0.0175 |
| System post seeding (t = 5 h) | 0.0625 | −0.0085 |

As shown from the data above, OD measurements five (5) hours after seeding that represent the media cell content, are lower than blank media measurement. This indicates that all cells are attached/trapped within the packed bed area. Hence, highly efficient seeding of the cell culture was demonstrated in the packed bed bioreactor seeding procedure.

Example 2: Monitoring *Cannabis* Cell Culture Proliferation in Packed Bed Bioreactors (in Process Control (IPC) Follow-Up)

The inventors of this invention developed methods to monitor the growth of the plant cells within the packed bed bioreactor during the bioreactor run. One optional method is described herein.

Wet weight of 8.5 g of *Cannabis indica* cell cultures were seeded as described in example 1 above. Seeding was conducted in biological triplicates, both in suspension cultures and in bioreactor systems (System 1, 2 and 3 in table 2 below represent triplicates).

Following seeding, bioreactor-based cell growth was conducted for a period of twenty-eight (28) days with an average perfusion rate of 190 ml/day. The total packed bed volume comprised 64% of Fibra-Cel™ carriers (which is a low amount relative to the number of carriers used in growth of animal cells in a packed bed bioreactor). The carriers were administered to allow plant cell culture expansion volume throughout the cultivation period. The pH set-point of the medium was 5.8, the Dissolved Oxygen (DO) set-point was 30%, and the temperature set-point was 25° C. These parameters were maintained by the system controller within the cell cultivation period. To characterize cell growth and viability, a few parameters were followed-up. These include medium uptake measurements and biomass. Growth rate was monitored using Glucose Consumption Rate per day (GCR/Day). GCR of cell culture increased from 46 to 129 (GCR/day) during cell proliferation stage. This data supports the biomass accumulation from 8.5 g to 18 g, which is a 2.1 folds increase.

Biomass accumulation data presented in Table 2 below suggests that packed bed bioreactor system is more efficient in growth of plant cells and medium usage relative to conventional parallel suspension cultivation of plant cells in shake flasks.

19

TABLE 2

| Biomass accumulation per volume comparison (gram/liter) | | | |
| --- | --- | --- | --- |
| | Suspension (shake flask) | Packed bed bioreactor | 3D/ Suspension ratio |
| System 1 | 372 | 669 | 1.80 |
| System 2 | 305 | 548 | 1.80 |
| System 3 | 55 | 207 | 3.76 |

Example 3: Plants Somatic Embryos Development in a Packed Bed Bioreactor

For plant somatic embryos differentiation and development, the selected plant cell cultures derived from germinated seeds are first seeded and cultivated as described in the Examples above. At the next step, phytohormones cytokinin TDZ at a concentration of 2 mg/l (Duchefa cat. T0916) and Auxin 2,4D at a concentration of 1 mg/l (Duchefa cat. D0911) are administered to the cultivated plant cells culture, optionally with growth factor such as 1 mg/l Gibberellic acid (Duchefa cat. G0907). Cell cultivation is conducted for two to four weeks at 25° C., until the globular stage is observed. High percentage carbon source content such as 0.15 Molar glucose and 0.25 Molar Sucrose is administered to the media to initiate or increase the efficiency of somatic embryos development and maturation (H. Lou, S. Kako, 1995). To eliminate the inhibitory effect of plant cell metabolites secreted on differentiation, high perfusion rates, above 1200 ml/day are used (Geovanny I. Nic-Can et al. 2015).

Example 4: Production of Carnosic Acid from *Rosmarinus officinalis* Cells

Carnosic acid is a natural benzenediol abietane diterpene found in *Rosmarinus officinalis* (rosemary) and in *Salvia officinalis* (common sage). It is usually used as an antioxidant preservative in food and nonfood products.

For production of Carnosic acid in packed bed bioreactor, *Rosmarinus officinalis* cells are first seeded and cultivated as previously described in Example 1 and 2 above. To maintain high cell culture proliferation and metabolite production potential, Phytohormones 0.5 mg/l Kinetin and cytokinin 1 mg/l TDZ are administered. Cell cultures are cultivated until stationary phase is reached, which is manifested in consistent carbon source consumption rate. Following the stationary phase, cells are harvested, lysed and the Carnosic acid is collected.

Example 5: Vanillin Production Using Specific Metabolite Precursors

Vanillin is the major component of vanilla bean extract. Vanillin is extensively used as a flavoring in food, beverages, cosmetics, and pharmaceuticals. For production of vanillin in packed bed bioreactor, *Vanilla Planifolia* cells are cultivated as described in Example 2 above. To enhance natural biosynthetic pathways, flavonoid precursors such as Tyrosine and phenylalanine at a 100-500 µM concentration are administered. Specific precursors of vanillin, such as 50-500 µM P-coumaric acid are added to the growth media. Once vanillin is accumulated in the cell culture, the cells can be lysed or rather harvested, and the desired compound is extracted from the growth media. Alternatively, common practice extraction methods such as Ethanol extraction may be used.

20

Example 6: *Cannabis* Plant Cell-Based Cannabinoid Production in Packed Bed Bioreactor

*Cannabis* callus cell cultures derived from sterile internode tissues were treated as described in examples 1-2 above. Following treatment cell cultures media was supplemented with stress inducing factors in a process referred to as Elicitation, additionally, to activate a generic secondary metabolite production in plant cells, the growth media included 100 µM Methyl Jasmonate (MeJA, Duchefa cat. M0918) for an activation period of three (3) days. Following three (3) days, perfusion was increased to remove MeJA from media and 15 mg/l chitosan (Sigma, cat. 448869) and 100 mg/l Olivetol as precursor (Sigma cat. 152633) were added to the media. To allow constant chitosan and olivetol concentration, perfusion was increased to 2 L/day.

Elicitation was conducted for a period of nine (9) days and fourteen (14) days. Post elicitation cultures were washed with control MS medium for a period of two (2) days. Harvest of cells from the bioreactor using mechanical forces and cell aggregate separation from the carriers was conducted. Chemical analysis of cell cultures Cannabinoid content was conducted using LC-MS/MS. Biomass yield, metabolite content and profile results indicate higher biomass and cannabinoids yield, both in total amount and profile, in packed bed bioreactors as illustrated in FIG. 6A-6B.

The results above suggest a beneficial effect for plant cell biomass accumulation and secondary metabolite production in a packed bed bioreactor compared to suspension cultures.

It should be clear that the description of the embodiments and attached Figures set forth in this specification serves only for a better understanding of the invention, without limiting its scope. It should also be clear that a person skilled in the art, after reading the present specification could make adjustments or amendments to the attached figures and above described embodiments that would still be covered by the current subject matter.

The invention claimed is:

1. A three-dimensional (3D) bioreactor for cultivating proliferating plant cells comprising:

at least one packed bed chamber configured to confine proliferating plant cells within it such that the proliferating plant cells remain as a stationary three-dimensional biomass phase during cultivation; and at least one container comprising a fluid media, the fluid media is configured to flow through proliferating plant cells stationary three-dimensional biomass phase;

vibrating arms functionally connected to the packed bed chamber, so as to allow vibrating of the proliferating plant cells for minimizing channeling effect and improving contact between the fluid media and the proliferating plant cells stationary biomass phase, and/or for harvesting said proliferating plant cells stationary three-dimensional biomass phase for either collecting the cells or for lysing the cells to obtain their content;

wherein the packed bed chamber is configured so that, after initial seeding, the plant cells are physically retained and do not circulate with the fluid media, thereby enabling in-situ development of large, stationary plant cell aggregates;

wherein, the flow of the fluid media through the proliferating plant cells stationary three-dimensional biomass phase allows transfer of compounds from the fluid media into the cells and from the cells into the fluid media in a low shear force environment within the at least one packed bed chamber thereby replicating the natural growth environment of the proliferating plant cells stationary three-dimensional biomass within the 3D bioreactor.

2. The bioreactor of claim 1, further comprising a monitoring unit for monitoring at least one parameter of the culturing conditions and media parameters.

3. The bioreactor of claim 2, wherein said at least one parameter monitored and/or controlled is selected from the group consisting of: pH, temperature, stirring velocity, flow rate, gases concentration, amino acids levels, vitamins levels, minerals levels, growth factors levels, dissolved oxygen levels, glucose levels, lactate levels, lactate dehydrogenase levels, NH.sub.3 levels, glutamate levels, and combinations thereof.

4. The bioreactor of claim 1, wherein said fluid media is a growth media that provides nutrients to the proliferating plant cells, and uptakes plant cells metabolites and secreted compounds from the plant cells into the growth media.

5. The bioreactor of claim 1, further comprising at least one inlet port to allow addition of gases and/or liquids and/or solid material into the 3D bioreactor during the cultivation of the proliferating plant cells.

6. The bioreactor of claim 1, further comprising at least one outlet port to allow removal of fluid media out from the 3D bioreactor during the cultivation of the proliferating plant cells for collecting metabolites secreted by the proliferating plant cells stationary biomass phase during the cultivation process and/or for removing plant's secreted compounds/metabolites and/or for balancing the fluid media parameters and/or for collecting cells after harvesting.

7. The bioreactor of claim 1, wherein said harvesting of the plant cells is obtained by combining enzymatic reaction and applying vibration force on the plant cells so as to lyse the cells and collect their content from the media and/or to lyse the plant cells from the stationary three-dimensional biomass.

8. The bioreactor of claim 1, wherein said packed bed chamber is either positioned within the container having the flowing fluid media or positioned outside the container having the fluid media and connected thereto by tubes that flow the fluid media through said proliferating plant cells stationary three-dimensional biomass phase.

9. The bioreactor of claim 1, wherein said packed bed chamber is divided into one or more sub-chambers by at least one perforated disk, such that each sub-chamber contains proliferating plant cells biomass cells either in a similar size or in gradient sizes according to the hole dimensions of the at least one perforated disk.

10. The bioreactor of claim 1, wherein said fluid media may be exchanged to either one of a differentiating media, a maturation media, and an elicitation media, and combinations thereof in any order, so as to allow a consecutive development of the plant cells and imitate the natural growth process of plant cells within the 3D bioreactor.

11. The bioreactor of claim 1, wherein said at least one packed bed chamber comprises carriers configured to allow said proliferating plant cells to grow within them and/or on top of them.

12. The bioreactor of claim 1, wherein said packed bed chamber is a separated chamber from said fluid media container and said plant cells stationary three-dimensional biomass phase is used in agriculture for seeding said stationary three-dimensional biomass phase to obtain plants or parts thereof.

13. The bioreactor of claim 1, wherein said plant cells stationary three-dimensional biomass phase is harvested for collecting compounds produced by said plant cells stationary three-dimensional biomass phase and/or for collecting the plant cells.

14. The bioreactor of claim 13, wherein said compounds or cells are used for industrial applications.

15. The bioreactor of claim 13, wherein said industrial applications are selected from: food manufacturing, medicaments, industrial applications, and cosmetic compositions.

16. The bioreactor of claim 1, further comprising a perfusion chamber containing a 3D packed bed substrate containing one or more macro carriers, microcarriers, or combinations thereof.

17. A method for cultivating proliferating plant cells for usage of the plant cells and/or compounds produced by said plant cells for medical, cosmetic, food tech, agriculture, and industrial applications using the bioreactor according to claim 1.

18. The bioreactor of claim 1, further comprising a controlling unit for controlling at least one parameter of the culturing conditions and media parameters.

19. A three-dimensional (3D) bioreactor for cultivating proliferating plant cells comprising:
   at least one packed bed chamber configured to confine proliferating plant cells within it such that the proliferating plant cells remain as a stationary three-dimensional biomass phase during cultivation; and
   at least one container comprising a fluid media, the fluid media is configured to flow through proliferating plant cells stationary three-dimensional biomass phase;
   a stirring mechanism functionally connected to said packed bed chamber and configured to blend the proliferating plant cells stationary biomass phase within said chamber, so as to rearrange the plant cells biomass and allow fluent flow of the fluid media through the plant cells, wherein said stirring mechanism comprises at least a large gear attached to a stirrer, said stirrer is positioned within said packed bed chamber, and a small gear attached to a handle;
   wherein the packed bed chamber is configured so that, after initial seeding, the plant cells are physically retained and do not circulate with the fluid media, thereby enabling in-situ development of large, stationary plant cell aggregates;
   wherein, the flow of the fluid media through the proliferating plant cells stationary three-dimensional biomass phase allows transfer of compounds from the fluid media into the cells and from the cells into the fluid media in a low shear force environment within the at least one packed bed chamber thereby replicating the natural growth environment of the proliferating plant cells stationary three-dimensional biomass within the 3D bioreactor.

* * * * *